United States Patent [19]

Kiske

[11] Patent Number: 4,821,568

[45] Date of Patent: Apr. 18, 1989

[54] METHOD AND APPARATUS FOR DETERMINING A MEASURABLE VARIABLE

[75] Inventor: Siegfried Kiske, Gross Grönau, Fed. Rep. of Germany

[73] Assignee: Draegerwerk, AG, Fed. Rep. of Germany

[21] Appl. No.: 116,364

[22] Filed: Nov. 2, 1987

[30] Foreign Application Priority Data

Nov. 20, 1986 [DE] Fed. Rep. of Germany ....... 3639666

[51] Int. Cl.$^4$ .......................... G08B 21/00; G01F 1/68
[52] U.S. Cl. ................................. 73/204.17; 340/606; 340/608
[58] Field of Search ............................ 73/204, 204.17; 364/510; 340/608, 606, 622, 59

[56] References Cited

U.S. PATENT DOCUMENTS

| 3,498,128 | 3/1970 | Calvet | 374/163 |
|---|---|---|---|
| 3,587,318 | 6/1971 | Belugou | 73/204 |
| 3,719,083 | 3/1973 | Morris et al. | 73/204 |
| 3,905,230 | 9/1975 | Calvet et al. | 73/204 |
| 4,068,526 | 1/1978 | Goldstein | 374/170 |
| 4,476,714 | 10/1984 | Barry et al. | 340/59 |
| 4,501,145 | 2/1985 | Boegli et al. | 73/204 |
| 4,770,037 | 9/1988 | Noir et al. | 73/204 |

FOREIGN PATENT DOCUMENTS 60-236078 11/1985 Japan .

Primary Examiner—Joseph A. Orsino
Assistant Examiner—Kenneth Tso
Attorney, Agent, or Firm—McGlew & Tuttle

[57] ABSTRACT

A method for determining a measurable variable of a flowing medium, in particular the flow velocity and/or the material properties, in which the temperature variation of a heated sensor is evaluated in an electronic measuring circuit for the determination of the variable. The measurement accuracy is improved in particular in the range of low flow velocities by heating the sensor with a heating pulse within at least one measurement period, and determining as a measured variable the time after which the sensor is cooled to at least a given temperature.

3 Claims, 3 Drawing Sheets

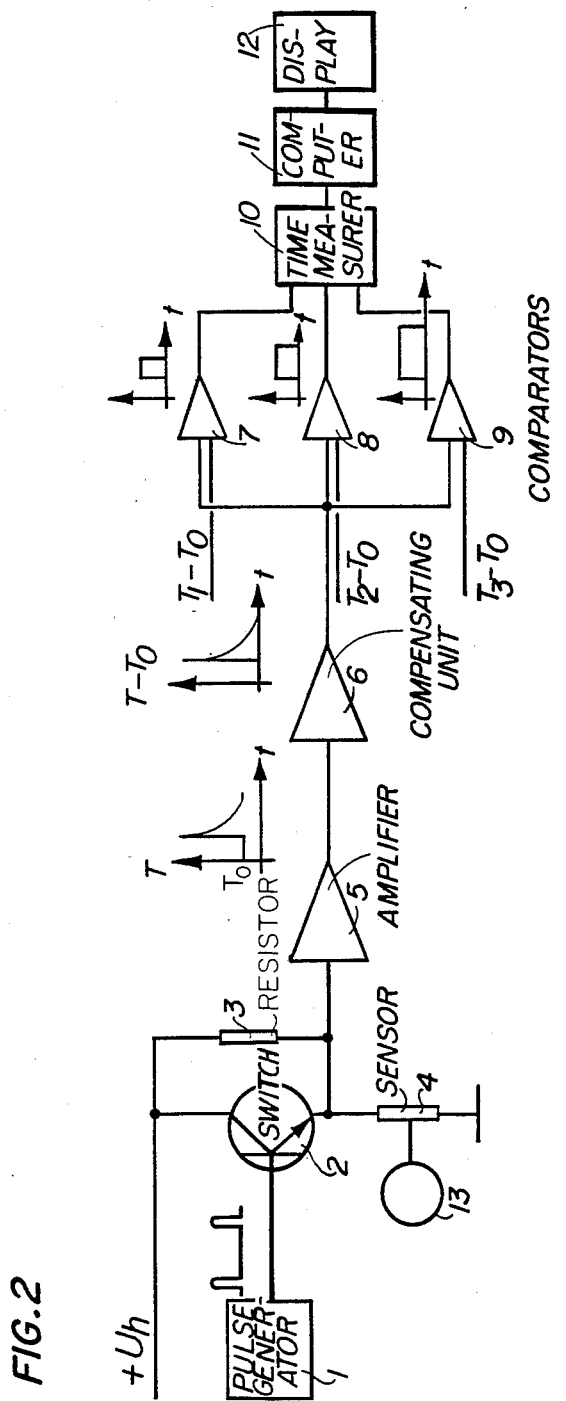

METHOD AND APPARATUS FOR DETERMINING A MEASURABLE VARIABLE

BACKGROUND OF THE INVENTION

Field of the Invention

This invention relates in general to measuring devices for flowing media, in particular to a new and useful method for determining measurable variable flowing media and for an apparatus for doing this.

The invention relates to blind measuring and detection and in particular to a method for determining a measurable variable of a flowing medium, in particular the flow velocity and/or the material properties, in which the temperature variation of a heated sensor is evaluated in an electronic measuring circuit for the determination of the variable.

From DE-OS No. 29 33 116 a device for measuring the breathing air flow is known where to sensors lying one behind the other at a distance are used, which are heated to constant temperature by a control circuit, the heating energy required therefore representing the measured variable.

Another known measuring device for determining the thermal conductivity of a gas mixture, which is described in German patent DE-PS No. 25 05 669, English patent No. 1544,818 permits the determination of the flow velocity and of the gas composition. For this purpose a resistance sensor is heated by electric current to a certain temperature, which is maintained by an appropriate control circuit. The current occurring in the sensor for the maintenance of the constant temperature constitutes the measured variable. The gas conduction in a flow channel is intermittent, with flow intervals and flowless intervals alternating at equal distances. In the flow interval, the measured variable constitutes a measure of the thermal conductivity and of the flow velocity of the medium. In the flowless interval, the thermal conductivity of the medium, e.g. of a gas mixture, is determined.

SUMMARY OF THE INVENTION

The problem formulation from which the invention proceeds is to avoid the known disadvantages of constant-temperature heating wire anemometry and to improve in particular the measurement when measuring flow velocity and/or the material properties of fluids, in particular at low flow velocities.

According to the invention, the sensor is heated with a heating pulse within at least one measurement section, and that, as a measured variable, the time is determined after which the sensor has cooled to at least a given temperature.

In contrast to the known constant-temperature method, the measurement problem is transferred from a complicated temperature measurement subject to many interference effects to a more precisely performable time measurement. Interfering side effects, as e.g. the heat conduction from the actual sensor to the feed lines or sensor mounts, have little effect. Besides, due to the pulsed heating clearly less current is consumed.

In practical execution, a series of heating pulses is used in each instance, and in one appropriate execution of the method the heating pulse is triggered in each instance when the sensor reaches a given temperature, so that in the case of fluctuating variables, for instance different flow velocities, variable pulse distances result.

Another desirable execution of the method includes using a series of equidistant heating pulses and the pulse distance is chosen great enough so that the limit value of the measured variable to be documented, for example the lowest flow velocity, still lies within a measurement section.

It has proven to be favorable to make the heating time, i.e. the duration of the heating pulses, very short in comparison with the length of the measurement sections. Appropriately the heating time is under 150 sec, while the lengths of the measurement sections are established advantageously between 1 and 50 msec. By the very short heating time, impairments of the heat transfer of the heated sensor by interfering side effects are further reduced and even avoided, because the cooling of the sensor is determined now essentially only by convective heat transport to the sweeping medium.

By periodical heating and cooling, the flow velocity can be inferred unambiguously if the material properties of the flowing medium are known. Since is has been proven by theoretical and experimental studies that the decrease in temperature due to forced convection occurs exponentially, the value of the exponent is a measure of the flow velocity.

For simultaneous determination of flow velocity and material properties, generally several linearly independent measurements are necessary, and this can be done e.g. by simultaneous determination of the "Abklingverhalten" (decay behavior) of several sensors of different design. This known method requires a complex construction of the sensors as well as long computing times for processor-controlled evaluation. In many cases moreover faultless measurement of the flow velocity at different composition of the flowing medium is necessary. This requires continuous calibration measurement to compensate the influence of the varying composition of the flowing medium. Such a compensation measurement for determining the influence of the gas properties can be carried out in a defined velocity state, generally at zero flow velocity. Such an intermittent measurement method has been described in DE-PS No. 25 05 669. An important prerequisite for this measurement is knowledge of the exact zero value of the flow velocity.

In further development of the invention, to determine zero flow the magnitude of the deviation from the exponential course of the temperature curve may be established, the zero value being present whenever the amount of the deviation from the exponential course reaches its experimentally determinable limit value. The deviation from the exponential "decay behavior" (Abklilngverhalten) is maximum at zero velocity; it decreases with increasing velocity and finally vanishes at a flow velocity which is greater than the diffusion velocity due to thermal conduction, so that the cooling curve changes over into the exponential course again.

As a measure of the magnitude of the deviation from the exponential course of the temperature curve; there may be chosen advantageously the temperatures for which, according to the exponential course of the cooling temperature curve, equal time differences $\Delta t_1 = t_2 - t_1$ and $\Delta t_2 = t_3 - t_2$ would result. This provides a determination of the ratio of the actually measured time differences $\Delta t_1$ and $\Delta t_2$ to the reaching of these temperatures, the limit value of this ratio establishing zero flow.

If, therefore, it has been established by measurement of the decay time ratio $\Delta t_1/\Delta t_2$ that the limit value of this ratio, and hence zero flow, has been reached, the course of the cooling temperature curve is determined exclusively by free convection. At fixed sensor properties the cooling rate will then depend only on the material properties of the flowing medium. Hence one can determine as measurable variables certain material properties, e.g. the gas composition. Such a measured value can then be used, possibly as a reference value, to compensate the influence of fluctuating compositions of the flow medium on the velocity measurement.

An appropriate measuring circuit for carrying out the method may be constructed so that an electronic switching element is provided which is connected to a pulse generator and connects the sensor, in its one switching position, to a heating voltage source and in its other switched position, to a resistance measuring arrangement. The reversal between the two switched states occurs rhythmically at equal distance or respectively when the sensor reaches a given resistance value. Comparators are provided for determining the time interval between the heating pulse and the reaching of the given resistance value.

As a function of the pulse sequence of the heating voltage source, advantageously they may be generated a series of equidistant spacing pulses, and in this case the variable to be determined can be determined by counting the number of spacing pulses lying between the heating pulse and the reaching of the given resistance value.

Accordingly it is an object of the invention to provide a method for determining a measurable variable of a flowing medium which comprises heating a sensor by imparting a heating pulse within at least one measurable period on evaluating the temperature variation of the heated sensor in an electronic measuring circuit and determining as a measurable variable the time after which the sensor is cooled to at least a given temperature.

The further object of the invention is to provide a device for determining a measurable variable of a flowing medium which includes means for imparting a heating impulse to a sensor of a given period and for evaluating the change in temperature of the sensor while the sensor cools to a pre-determined temperature.

A further object of the invention is to provide an electronic sensor for determining variables of a fluid which includes a pulse generator for generating a pulse signal having equal length measurements periods, means for providing heating pulses to a sensor connected to the pulse generator switch means for actuating both the pulse generator and the heating of the sensor so that a heating voltage is applied to the sensor over a period of time and including means for measuring the voltage at the sensor for evaluating a voltage drop thereof, and for subsequently evaluating the voltage change in comparators over a period of time.

A further object of the invention is to provide a device for 10 evaluating fluids which is simple in design, rugged in construction and economical to manufacture. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

FIG. 2 is a schematic measuring circuit for the execution of the method.

GENERAL DESCRIPTION OF THE PREFERRED EMBODIMENTS

Figure 1:
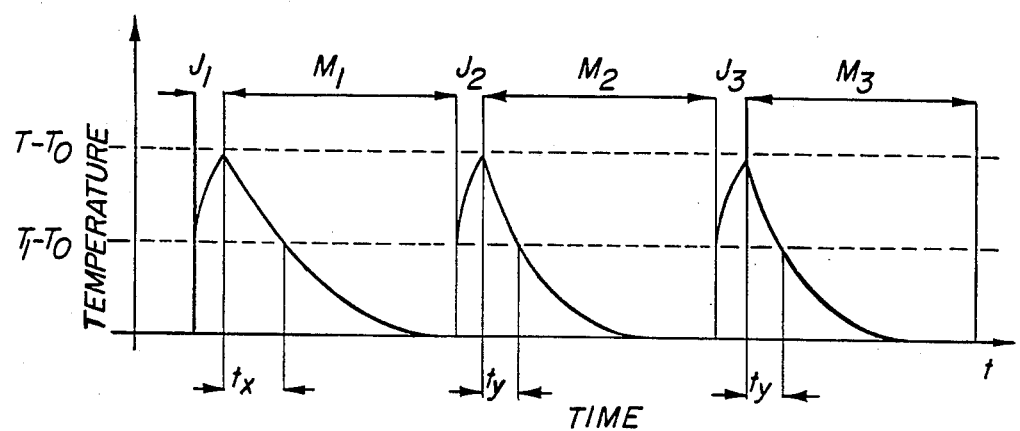
FIG. 1 is a diagram of a series of heating pulses.

Referring to the drawings in particular the invention therein comprises a method and an apparatus for determining a measurable variable of a flowing medium such as a gas for evaluating a temperature variation of a sensor 4, which is supplied by a pulse generator for generating a pulse signal with equal length measurement sections or periods in which through a switch 2, provides periods of heating of the sensor 4. Means are also provided for measuring the voltage at the sensor 4 including a meter 13 and a connection to amplifiers 5 and 6 and comparator 7, 8 and 9 which are evaluated by time measuring device 10 and computer 11 and displayed at a display device 12.

In FIG. 1 shows a series of equidistant successive heating pulses $J_1$, $J_2$, $J_3$, always located at the beginning of the measurement sections $M_1$, $M_2$, $M_3$. By these heating pulses $J_1$, $J_2$, $J_3$ the sensor is heated to a temperature $T-T_0$ above the ambient temperature $T_0$, for example to 300° C. After termination of the heating pulse, the original heating temperature $T-T_0$ decays to the given value $T_1-T_0$. The time $t_x$ required for this depends on the flow velocity at the sensor. From the times $t_x$, $t_y$, determined by time measurement, the flow velocity of the medium sweeping the sensor can be inferred with great accuracy. $t_x$ means a lower flow velocity in section $M_1$, while in the sections $M_2$ and $M_3$ the flow velocities are equal but higher than flow velocities in section $M_1$, expressed the velocities of section $M_2$ and $M_3$ are by $t_y$, exist in FIG. 1.

For satisfactory performance of the measurements the internal thermal resistance of the sensor is to be much smaller than the resistance for the heat transfer to the surrounding medium. For gases this is achieved with high accuracy if the sensor is made of the usual material, for example platinum or tungsten wire of a diameter <0.05 mm.

If the duration of the heating pulses $J_1$ ... is chosen sufficiently short, the maximum temperature of the sensor remains independent of the flow velocity and of material properties. The total length of the measurement sections $M_1$ ... is to be sufficiently long, so that it is always ensured that upon cooling the sensor will assume the given temperature $T_1-T_0$.

In the embodiment according to FIG. 1, measurement sections $M_1$, $M_2$, $M_3$ of equal length in each instance are indicated. This means that heating starts again only after completion of the entire measurement section. For some purposes of use (increased frequency of measurement), however, it appears to be more desirable to trigger the heating pulse, at variable length of the measurement sections, when the given temperature $T_1-T_0$ is reached.

The measuring circuit according to FIG. 2 contains a pulse generator 1 by which, via a transistorized switch 2, the pulse sequence illustrated in FIG. 1 with equal length of the measurement sections and the triggering of the heating pulses $J_1$, $J_2$ ... are controlled. At every pulse the pulse generator 1 closes the transistorized switch 2, so that in this switched position the heating voltage $U_h$ is applied to the sensor 4. During the interpulse, the transistorized switch 2 cuts off, and in this position the measurement of the resistance is carried out at the sensor 4. The measuring current fed into sensor 4 via resistor 3 is chosen so great that no notable temperature increase of the sensor takes place, but an evaluable voltage drop at the sensor 4 occurs, as a measure of the resistance and hence of the temperature.

Figure 3:
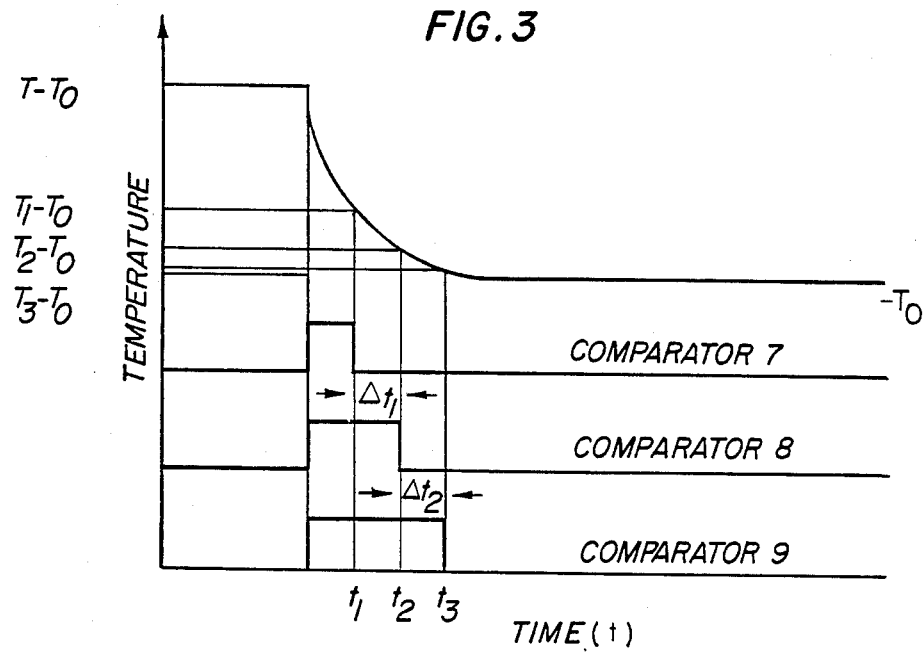
FIG. 3 is a representation of signals occurring in the measuring circuit.

The output signal of sensor 4 representing the sensor temperature T not adjusted for the influence of the ambient temperature is amplified in an amplifier 5 and the signal is conditioned at compensation unit 6 for the influence of the ambient temperature such that compensation unit 6 outputs a signal representative of the sector temperature T less the ambient temperature $T_0(T-T_0)$. The conditioned signal $(T-T_0)$ is supplied to an evaluating unit comprising three comparators 7, 8, 9. The then following time measuring unit 10 determines the length of the times $t_1, t_2 \ldots$ serving as measured variables. As can be seen in FIG. 3 $t_1$ is the time it takes the sensor temperature to reach the temperature $T_1-T_0$, $t_2$ is the time it takes the sensor temperature to reach the temperature value $T_2-T_0$ and $t_3$ is the time it takes the sensor to reach the temperature $T_3-T_0$.

A then following computing unit 11 serves to transform the time values into the respective values of flow velocity or material properties, which are read out in a display unit 12.

FIG. 3 shows the decaying of the heating temperature from $T-T_0$ to three given temperature values $T_1-T_0$, $T_2-T_0$, $T_3-T_0$, the times required for this being determined with the output of comparators 7, 8, 9. The comparators 7, 8 output signal for the determination of the time difference $\Delta t_1 = t_2 t_1$, while the comparators 8, 9 output signals for the determination of the time difference $\Delta t_2 = t_3 - t_2$.

Figure 4:
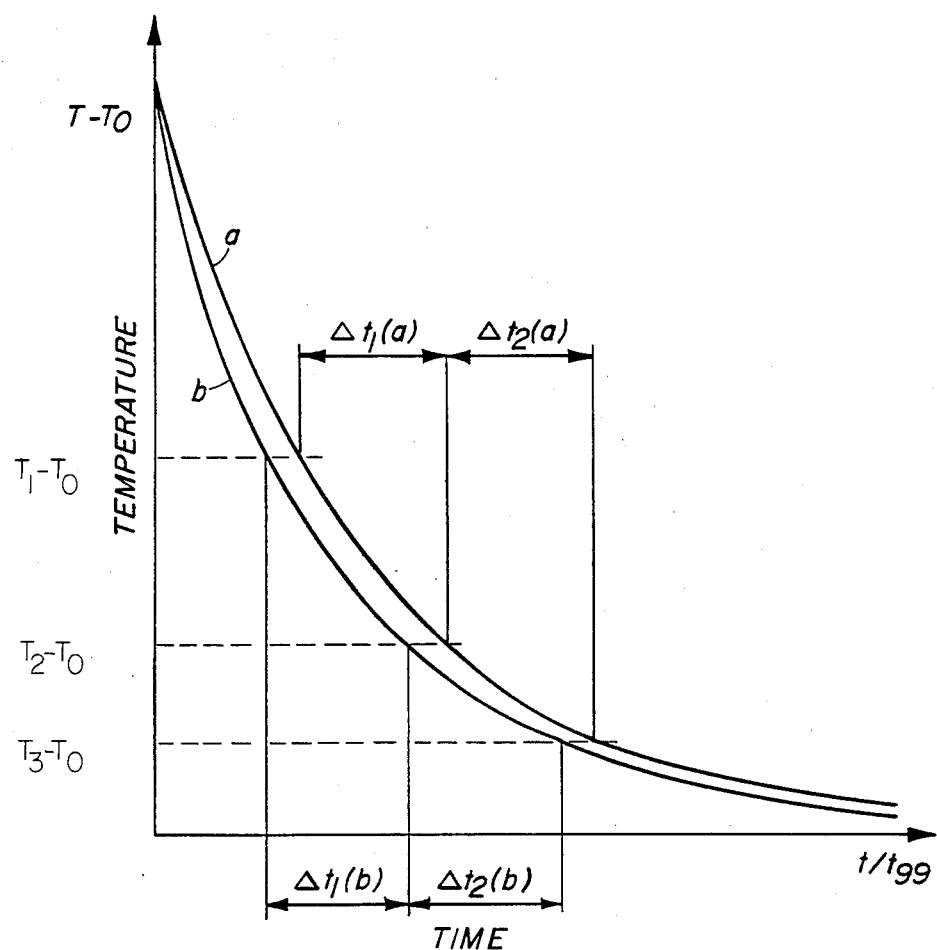
FIG. 4 is a decay curve at zero velocity.

In order that besides the flow velocity one can check and determine in a flowless interval at zero flow velocity also additional material properties, the time response of the cooling curves must be monitored: At high flow velocities the decay behavior of the cooling curves is strictly exponential, as represented by the cooling curve a. At vanishing flow velocity the cooling curve follows a non-exponential course according to cooling curve b (FIG. 4).

As a measure of the magnitude of the deviation from the exponential decay two time differences $\Delta t_1$ and $\Delta t_2$ initially of equal duration during flow condition, are measured, namely the times which the sensor needs to decay from a temperature $T_1$ over the ambient temperature $T_0$ to the temperature $T_2-T_0$, where in the exponential course there is to apply $$K \times (T_1 - T_0) = T_2 - T_0$$

and further from the temperature $T_2-T_0$ to the temperature $T_3-T_0$ with the same coefficient K $$T_3 - T_0 = K \times (T_2 - T_0) = K^2 \times (T_1 - T_0)$$

In the case of exponential course (curve a) the times $\Delta t_1$ (a) and $\Delta t_2$ (a) are equally long. Their ratio will be 1. At velocities in the range of zero flow different time differences occur, whose quotient $\Delta t_1 : \Delta t_2$ must be monitored. When an experimentally determinable limit value of the ratio $\Delta t_1$ (b): $\Delta t_2$ (b) is reached, it is to be assumed that zero flow exists. After this has been established, i.e. after the heat exchange between the sensor and the surrounding medium depends now only on the thermal conductivity of the gas and hence on material properties but not on the convection brought about by a flow, material properties can be inferred by time measurement for the cooling to a given temperature.

An appropriate execution of the measuring method can provide for example that after several measuring sections $M_1 \ldots$ the flow of the medium to be measured is turned off in the flow channel and zero flow is established in the stated manner while noting the deviation from the exponential decay behavior. In a then following measurement section, material properties, for example the constant composition of a gas flow, are checked and if desired taken into account mathematically for the continued measurement of the flow velocity.

An appropriate application of the novel measuring method for the determination of zero flow resides, inter alia, in monitoring artificial respiration. In periodical flow processes, as they occur in artificial respiration, in which zero velocity phases appear regularly, it is possible, by routine checking of the amount of deviation from the exponential decay behavior, to establish the velocityless state automatically. An changes in gas composition can be picked up as well The measuring method can appropriately be carried out also with several sensors of identical or different design, depending on the existing facts While specific embodiments of the invention have been shown and described in detail to illustrate the application of the principles of the invention, it will be understood that the invention may be embodied otherwise without departing from such principles.

What is claimed is:

1. A method for determining a no flow condition of a medium having a flow condition and a no flow condition, comprising: heating a sensor by imparting a heating pulse, the sensor cooling exponentially during a flow condition over one measurement period, and the sensor cooling non-exponentially during a no flow condition; evaluating the time after which the sensor is cooled to at least a pre-determined temperature, detecting the amount of deviation from an exponential course of a cooling temperature curve; and establishing a no flow condition when the amount of deviation from the exponential course reaches a limit.

2. The method according to claim 1, wherein as a measure of the amount of deviation from the exponential course of the cooling temperature curve, temperature $T_1$, $T_2$ and $T_3$ are chosen in such a way that during a flow condition, the time period for the sensor to cool form $T_1$ to $T_2$ is equal to the time period for the sensor to the cool form $T_2$ to $T_3$; during a measuring period, time $\Delta t_{1b}$ for the sensor to cool from $T_1$ to $T_2$ and time period $\Delta t_{2b}$ for the sensor to cool from $T_2$ to $T_3$ are measured, the ratio of $\Delta t_{1b}$ to $\Delta t_{2b}$ is determined, a no flow condition is established when the ratio reaches a limit.

3. A method for detecting a no flow condition of a medium having a flow condition and a no flow condition, comprising the steps of:

during a measurement period, heating a sensor by imparting a heating pulse and allowing the sensor to cool, the sensor cooling in an exponential manner during a flow condition and cooling in a non-exponential manner during a no flow condition;

choosing temperature $T_1$, $T_2$ and $T_3$ during a flow condition such that the time period for the sensor to cool from $T_1$ to $T_2$ is equal to the time period for the sensor to cool from $T_2$ to $T_3$;

repeating the heating and cooling of the sensor to provide successive measurement periods;

determining the ratio of the time period for the sensor to cool from $T_1$ to $T_2$ to the time period for the sensor to cool from $T_2$ to $T_3$ during the successive measurement periods;

detecting the ratio of the time period for the sensor to cool from $T_1$ to $T_2$ to the time period for the sensor to cool from $T_2$ to $T_3$ approaching a limit value;

establishing a no flow condition when said approaching is detected.

* * * * *